(12) United States Patent
Innocenzi

(10) Patent No.: US 7,836,880 B2
(45) Date of Patent: Nov. 23, 2010

(54) PRESSURIZED METERED DOSE INHALER SYSTEM

(76) Inventor: Kevin Innocenzi, 1243 Oakwood Dr., Arcadia, CA (US) 91006

( * ) Notice: Subject to any disclaimer, the term of this patent is extended or adjusted under 35 U.S.C. 154(b) by 914 days.

(21) Appl. No.: 11/654,178

(22) Filed: Jan. 17, 2007

(65) Prior Publication Data

US 2007/0277817 A1    Dec. 6, 2007

(51) Int. Cl.
*A61M 11/00* (2006.01)
(52) U.S. Cl. .............................. 128/200.23; 128/203.12; 128/200.14; 222/36; 222/38
(58) Field of Classification Search ............ 128/200.14, 128/200.24, 200.23, 203.12, 203.15, 203.21, 128/205.23; 222/32, 36, 38; 116/311, 312, 116/307, 317, 318
See application file for complete search history.

(56) References Cited

U.S. PATENT DOCUMENTS

| | | | |
|---|---|---|---|
| 4,907,835 A * | 3/1990 | Salters | 296/1.09 |
| 2002/0195102 A1* | 12/2002 | Rand et al. | 128/200.23 |
| 2004/0222237 A1* | 11/2004 | Blacker et al. | 222/36 |
| 2004/0255936 A1* | 12/2004 | Urbanus | 128/200.23 |
| 2006/0225733 A1* | 10/2006 | Malhotra et al. | 128/200.23 |
| 2007/0210102 A1* | 9/2007 | Stradella et al. | 222/36 |

* cited by examiner

*Primary Examiner*—Justine R Yu
*Assistant Examiner*—Valerie Skorupa
(74) *Attorney, Agent, or Firm*—Roberta D. German

(57) ABSTRACT

The present invention provides a pressurized metered dose inhaler (pMDI) system, comprising a transparent or partially transparent canister which permits a patient to view the amount of medicament remaining in the pMDI system. The system of the present also comprises a dose counter which counts a dose when a dose is dispensed. The present invention provides a pMDI system which is improved over those currently used for treating respiratory diseases.

18 Claims, 4 Drawing Sheets

PRESSURIZED METERED DOSE INHALER SYSTEM

Throughout this patent application various publications are referenced. The disclosures of these publications in their entireties are hereby incorporated by reference into this patent application in order to more fully describe the state of the art to which this invention pertains.

FIELD OF INVENTION

The present invention relates to a pressurized metered dose inhaler system comprising a transparent canister for viewing the amount of a medicament remaining in the canister, and a mechanical dose counter for monitoring the number of dispensed doses dispensed.

BACKGROUND OF THE INVENTION

Pressurized metered dose inhalers (pMDI) are commonly used by patients for self-administered treatment of respiratory diseases, such as asthma and chronic obstructive pulmonary disease (COPD). The pMDIs are versatile because they are adaptable for filling with various propellants, and dry or liquid medicaments. They are also convenient, since they are easily portable. However, despite regular use of the pMDIs, patients often experience serious respiratory distress that can be life-threatening. This is in part because patients are sometime unaware they have depleted the medication in their pMDIs and instead self-administer the propellant. Patients cannot visually monitor the amount of medication remaining in their pMDIs because the metal canisters are not transparent. And most pMDIs are not equipped with a dose counter. In order to track the number of doses remaining in the pMDI, patients can manually record the number of doses they have administered, shake the pMDI to determine the amount of medication remaining, or float the canister in water. None of these methods is reliable. It is estimated that only 8% of pMDI users accurately track the doses they administer. There exists a need for a pMDI system that will permit patients to accurately assess the amount of medication remaining in the canister. The present invention provides a pMDI system having a transparent canister to permit visualization of the amount of medication remaining. The present invention also provides a pMDI system equipped with a dose counter that is driven to count a dose when a dose is dispensed.

DETAILED DESCRIPTION OF THE INVENTION

The present invention provides a pressurized metered dose inhaler (pMDI) system, which permits a patient to more accurately determine the amount of medicament remaining in the pMDI system and monitor the number of doses dispensed. The present invention provides a pMDI system which is improved over those currently used for treating respiratory diseases, including: asthma; chronic obstructive pulmonary disease (COPD); bronchitis; and emphysema.

Canister

Figure 1:
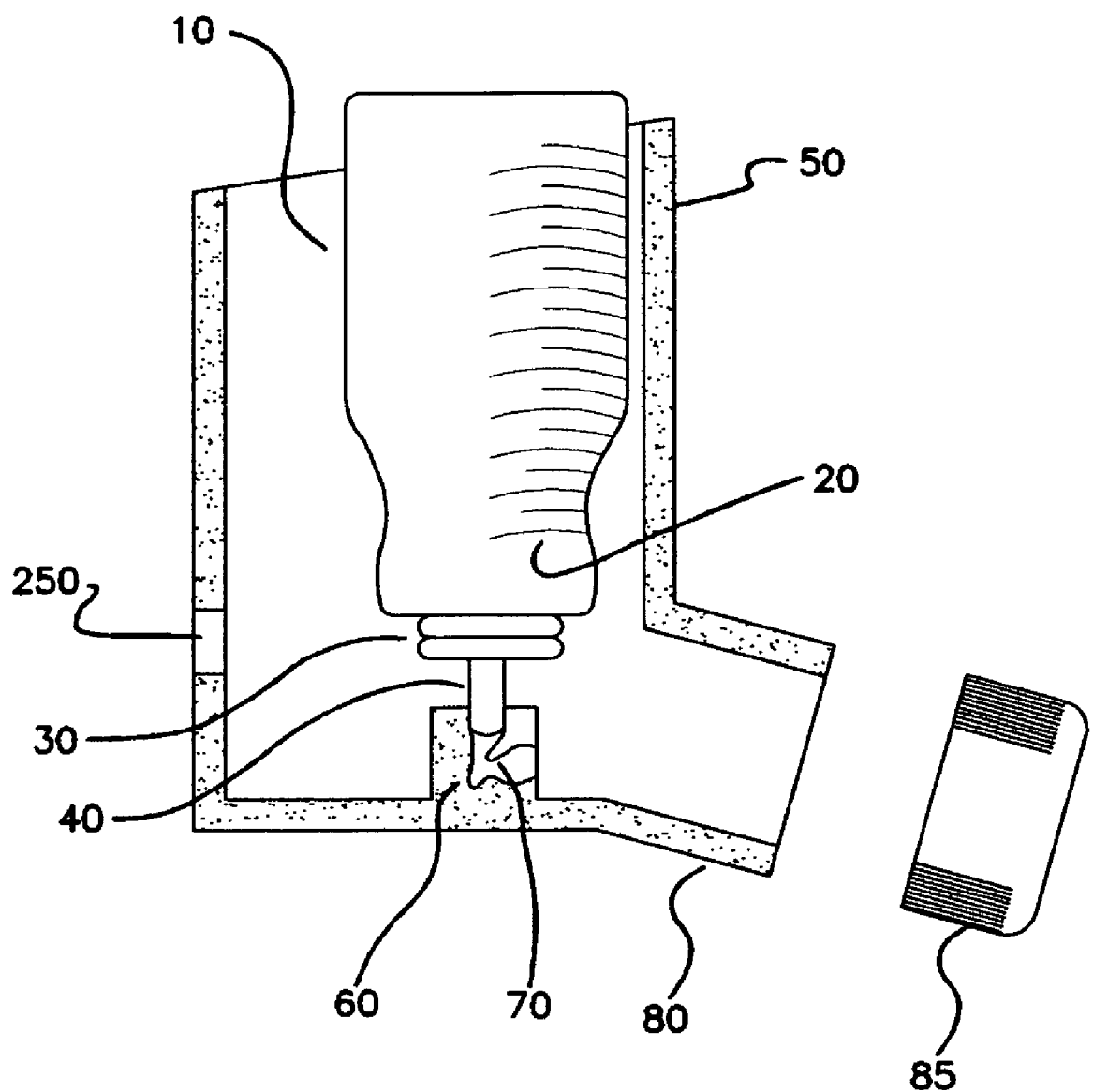
FIG. 1 is a side elevational view of: a canister, closed at one end with a metered dose assembly, placed in a valve-stem down position in a housing; and a dust cap.

FIG. 1 shows a canister (10) placed in a housing (50). For the sake of clarity, FIG. 1 does not show the dose counter of the present invention. The pMDI system of the present invention comprises a canister (10) which is formed from a transparent or partially transparent material. The transparent or partially transparent material can be plastic, glass, or plastic-coated glass. The plastic or glass can be material which does not react with a propellant gas or medicament, and is capable of withstanding vapor pressures of about 85 psi (pounds per square inch). The transparency and color of the plastic or glass permits visualization of the medicament inside the canister, and can be: clear and colorless; clear and colored; partially clear and colorless; or partially clear and colored. The plastic can be polymethyl methacrylate (PMMA), polyethylene terephthalate (PET), polystyrene, or polycarbonate. The plastic can be acrylic glass or Lexan™. The glass can be Double-Tough Pyrex™ (DTP).

The canister can have measurement markings (20) to permit an estimated measurement of the amount of medicament and/or propellant remaining in the canister (10). The measurement markings (20) can be calibrated to any metric or non-metric units of volume, weight and/or dose. The markings (20) can be graduated markings. The markings (20) can be etched, painted, or raised.

It is well known in the art how to select and make a canister (10) having the appropriate shape, size and dimensions for use in a pressurized metered dose inhaler system for dispensing medicaments used to treat respiratory diseases. For example, suitable cross sectional shapes include rectangular, circular, elliptical, or concavoconcave. The base of the canister (10) can be concave.

The canister (10) can be filled with medicament for treating a respiratory disease and at least one propellant gas. The respiratory diseases include asthma, chronic obstructive pulmonary disease (COPD), bronchitis, and emphysema. The canister can be filled with at least one medicament (active ingredient) typically used to treat respiratory diseases, including: albuterol, albuterol sulfate, beclomethasone dipropionate, bitolterol mesylate, cromolyn sodium, dexamethasone sodium (phosphate), epinephrine (e.g., as nitrate or hydrochloride), epinephrine bitartrate, flunisolide, fluticasone propionate, ipratropium bromide, isoetharine mesylate, isoproterenol hydrochloride, isoproterenol sulfate, metaproterenol sulfate, nedocromil sodium, pirbuterol acetate, salmeterol xinafoate, triamcinolone acetonide, and/or terbutaline sulfate. The medicament can be mixed with a cosolvent and/or expedient. The medicament can be mixed with a dispersing agent which acts to disperse particles of the medicament and maintains a suspension of the medicament. The dispersing agent can ensure dispensing uniform doses of the medicament. The dispersing agent include: oleic acid; sorbitan oleate; sorbiton trioleate; sorbiton sesquioleate and lethicin.

The propellant gas can be one or any combination of a chlorofluorocarbon (CFC) such as: trichloromonofluoromethane (CFC-11); dichlorodifluoromethane (CFC-12);

and/or dichlorotetrafluoroethane (CFC-114). The propellant gas can be one or a combination of a hydrofluoroalkane such as: HFC-134a (also known as 1,1,1,2-tetrafluoroethane); and/or HFC-227 (also known as 1,1,1,2,3,3,3-heptafluoropropane).

The internal surface of the canister (10) can be coated and/or impregnated with a surfactant to prevent the medicament from sticking to the canister surface (stabilizes the suspended medicament). The surfactant can be any one or a combination of: anionic (e.g., oleic acid); zwitterionic (e.g., lecithin); non-ionic (e.g., sorbitan or trioleate); and/or oligolactic acid.

Valve Assembly

The pMDI system of the present invention comprises the canister (10) closed at one end with a metered dose valve assembly (30) (FIG. 1). The valve assembly (30) comprises a valve stem (40). The valve assembly (30) is designed to dispense a metered amount of the medicament when the valve assembly (30) is actuated. The valve assembly (30) is actuated by moving the valve stem (40) toward the canister (10). The medicament is dispensed through the valve stem (40). It is known in the art how to select and make the various components of the valve assembly (30) based on the type of propellant gas and/or medicament used to fill the canister (10). For example, the valve assembly (30) can be based on CFC-11, CFC-12 and/or CFC-114. The valve assembly (30) can be based on HFC-134a and/or HFC-227ea. Valve assemblies appropriate for use with HFC propellants are well known in the art (see for example, U.S. Pat. Nos: 4,744,495; 5,190,029; 5,427,282; and 6,036,942)

Housing

The pMDI system of the present invention comprises a housing (50) which receives and holds the canister (10) in a valve stem-down position (FIG. 1). The housing (50) comprises an orifice box (60) for securely holding the valve stem (40). The housing (50) comprises an internal stop (70) for actuating the valve stem (40) to dispense the medicament. The housing (50) comprises an integral off-set mouthpiece (80) for directing the dispensed medicament into the patient's mouth. The housing (50) can be shaped and sized to fit in the palm of a patient's hand (child, teen, or adult). The housing (50) can be formed from plastic, and can be transparent, partially transparent or opaque. It is well known in the art how to select the material, shape and dimensions of the housing (50). An example of a housing to receive a canister with a metered dose valve is disclosed in U.S. Pat. No. 5,564,414.

The canister (10) is placed in the housing (50) in a valve stem-down position. The valve stem (40) is inserted into the orifice box (60) and rests on the internal stop (70). To dispense the medicament, the base of the canister (10) is depressed with sufficient pressure to move the canister (10) in a downward direction. The valve stem (40) is actuated by the downward motion of the canister (10), and the medicament and propellant in the canister (10) is released as a vapor through the valve stem (40) and through the orifice box (60) and through the off-set mouthpiece (80). The canister (10) returns to its original position when the downward pressure is released.

Dose Counter

Figure 2:
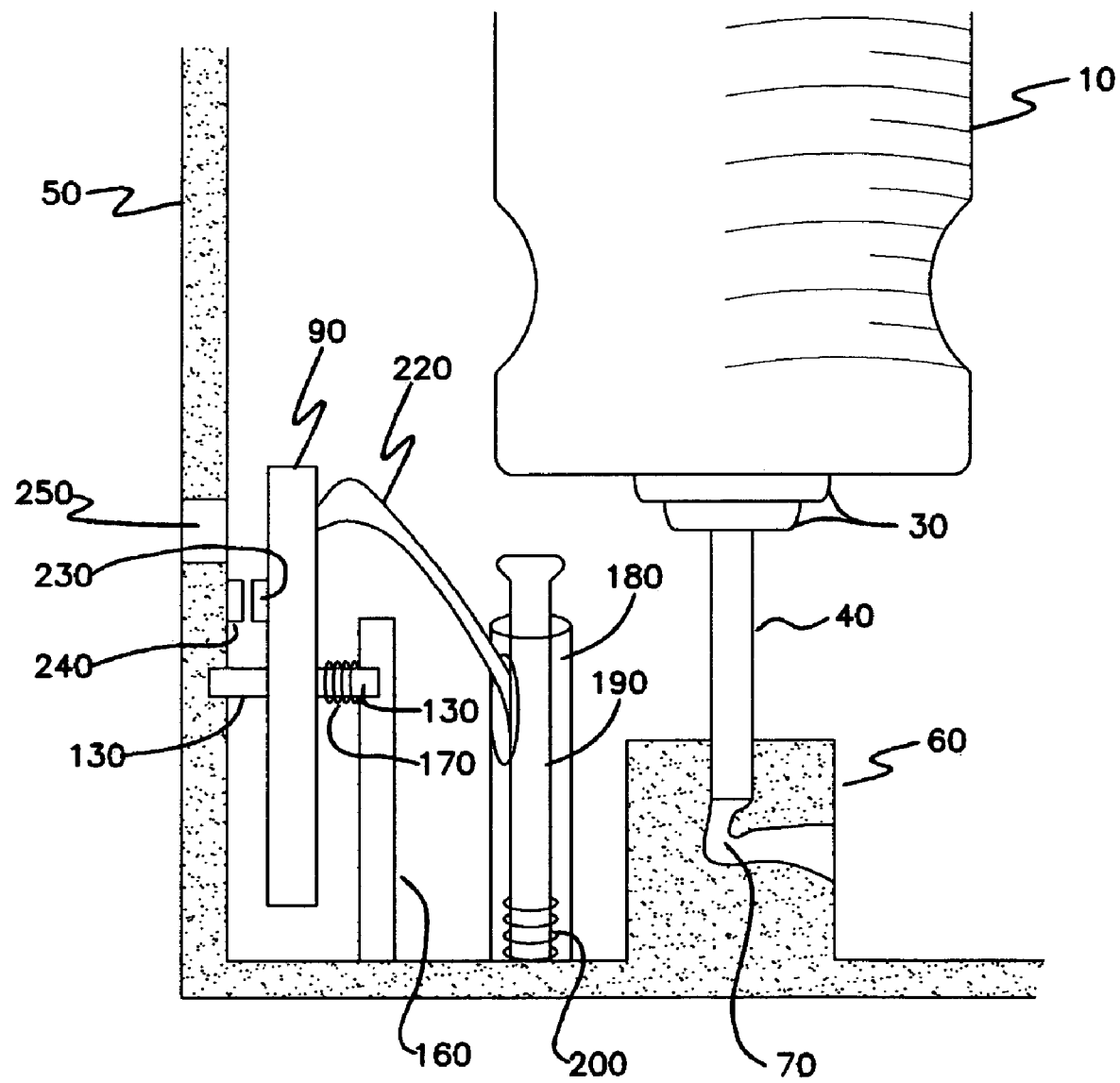
FIG. 2 is a partially broken away side elevational view enlarged to show the dose counter of the present invention and a canister.

The pMDI system of the present invention comprises a dose counter which counts the number of doses dispensed from the pMDI system (FIG. 2). The dose counter counts a dose when the metered valve assembly is actuated to dispense a dose. The dose counter can be a count-down or count-up counter. The dose counter can be mounted on the inside of the housing (50). The dose counter is mounted in such a way that it does not interfere with actuating the metered dose valve assembly (30). In the pMDI system of the present invention, the dose counter permits the patient to more accurately monitor the number of doses dispensed.

Dose Counter—Rotation Means

Figure 3A:
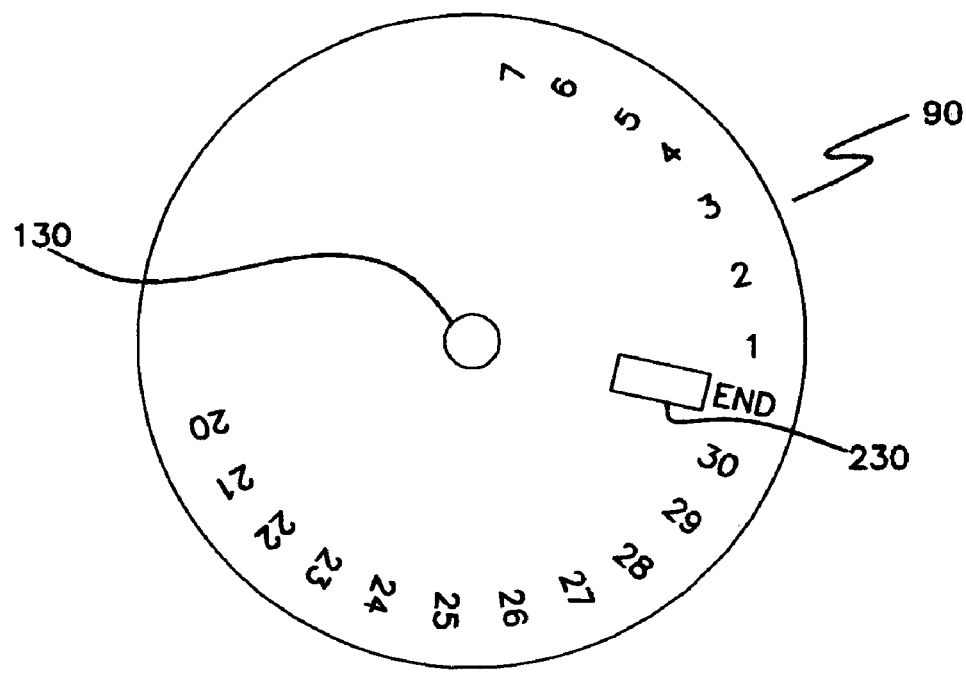
FIG. 3A is an elevational view of the front side of the wheel with alpha-numeric characters.
Figure 3B:
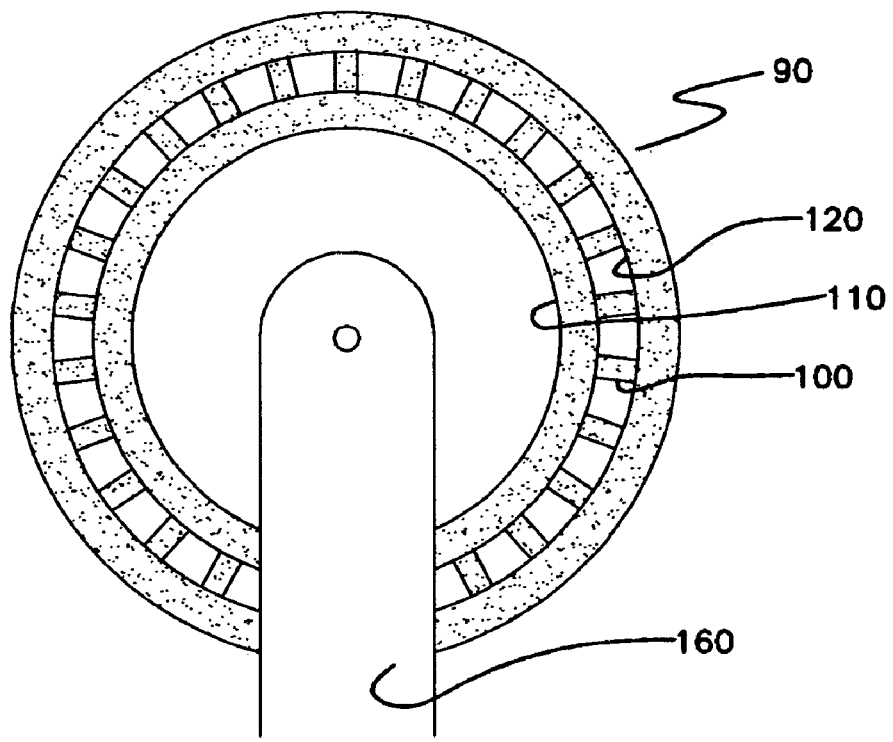
FIG. 3B is an elevational view of the back side of the wheel with gear teeth arranged between an inner and outer raised rail, with the wheel mounted on the stabilizer bar.
Figure 4A:
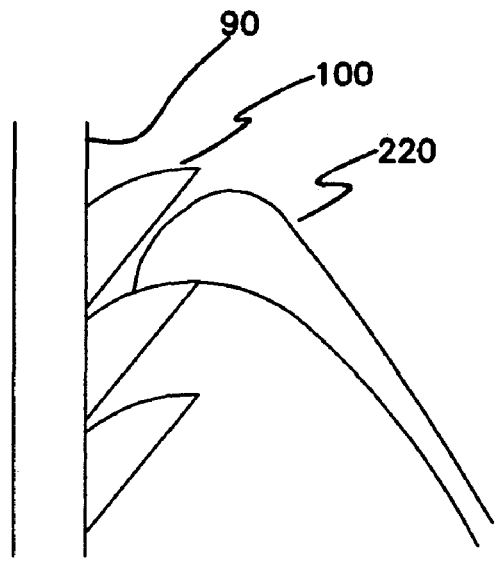
FIG. 4A is cut-away side view of the wheel enlarged to show the gear teeth and the pawl engaged with a gear tooth.

FIGS. 2, 3 and 4 show one embodiment of the dose counter. The dose counter comprises a wheel (90) (FIG. 2) having a plurality of gear teeth (100) arranged between an inner raised rail (110) and an outer raised rail (120) on the face of the wheel (90) (FIG. 3B). The gear teeth (100) are arranged perpendicular to the wheel (90) between the inner and outer raised rails (110 and 120, respectively). A side view of the shape of the gear teeth (100) is shown in FIG. 4A. The number of gear teeth (100) is determined by the number of doses to be dispensed by the pMDI system. The wheel (90) is rotatably mounted by an axle (130) (FIG. 2). One of the axles (130) is mounted in a recess (140) in a side wall of the housing (50) (FIG. 2). The other axle (130) is mounted in a recess or hole (150) in a stabilizer bar (160) which is rigidly attached to the floor of the housing (50) (FIG. 2). One of the axles (130) is received by an axle compression spring (170) (FIG. 2).

Dose Counter—Counting Means

The wheel (90) has alpha-numerical characters depicted on the front of its face which correlate with the number of doses of medicament to be dispensed from the pMDI system. The characters are depicted near the periphery of the wheel (FIG. 3A).

The characters can be a range of numerals typically used for pMDIs, such as from 0 to 30, or 0 to 50, or 0 to 60, or 0 to 100. Alternatively, the numeral characters can range from 30 to 0, 50 to 0, 60 to 0, or 100 to 0. Successive or skipped characters can be depicted on the wheel (FIG. 3A). The numeral range corresponds with the maximum number of doses to be dispensed from the pMDI system. The wheel (90) can also have alphabet characters depicted on its face. The alphabet characters can form words such as "end", "empty", "stop", or "halt" which indicate termination of the number of doses to be dispensed from the pMDI system. The words can be "replace" or "re-order" which indicate the pMDI is nearly empty and notifies the patient to obtain a new pMDI system. The counter can be connected with an audible alarm which sounds when the metered dose valve assembly is actuated, or when a predetermined number of doses has been dispensed, or when the last dose is dispensed.

Dose Counter—Reverse Rotation Prevention Means

Figure 4B:
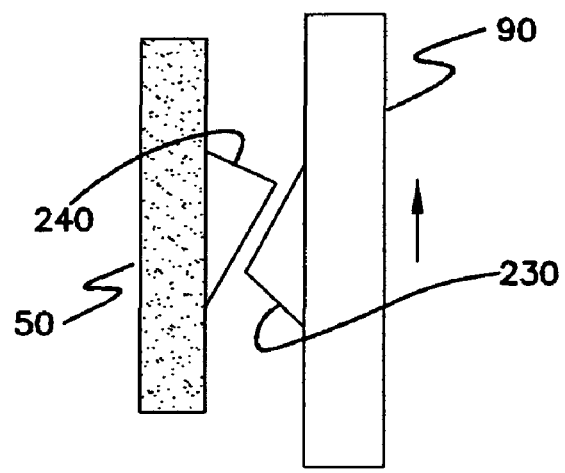
FIG. 4B is a cut-away side view of a housing stop projection and a wheel stop projection.
Figure 4C:
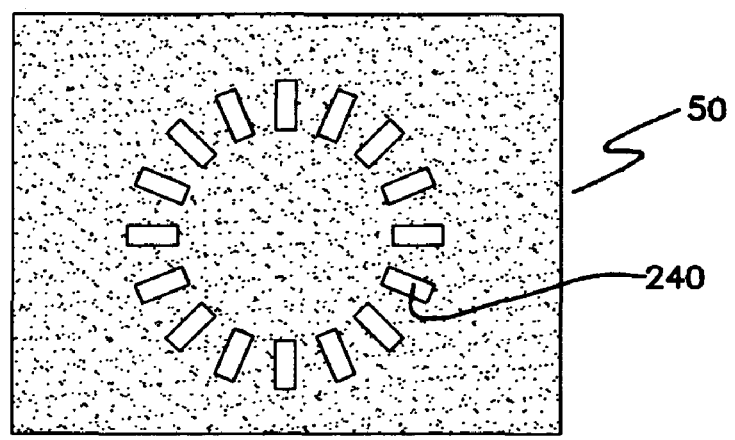
FIG. 4C is a front elevational view of one inner wall of the housing having a plurality of housing stop projections.

The back side of wheel (90) has a wheel stop projection (230) (FIG. 3A). A plurality of housing stop projections (240) are mounted on the inner wall of the housing (50). The housing stop projections (240) can be arranged in a circle as shown in FIG. 4C. The cross-sectional shape of the wheel stop projection (230) and a housing stop projection (240) is shown in FIG. 4B. As the wheel (90) turns in one direction, the axle compression spring (170) permits the wheel stop projection (230) to move pass one of the housing stop projections (240), and contact between the wheel stop projection (230) and the housing stop projection (240) prevents the wheel (90) from rotating in the opposite direction.

Dose Counter—Pawl Drive Means

The dose counter also comprises a cylinder (180) rigidly attached in a vertical, or approximately vertical, position to an internal floor of the housing (50) (FIG. 2). A rod (190) is slidably disposed in the cylinder (180), and the rod (190) is biased toward an upward position by a rod compression spring (200). The top of the rod (190) can be enlarged or shaped to increase the contact area between the top of the rod (190) and the canister (10). The enlarged area can be coated with and/or formed from a non-slip material. The rod (190) is connected with an angled, elongated, flexible pawl (220) (FIG. 2). The end of the pawl (220) is adapted to engage a gear tooth (100) (FIG. 4A). The pawl (220) is slidably disposed in a slit in the cylinder (190) (FIG. 2). The pawl (220) can be formed from a material that is flexible to permit it to bend and then return to its original position. The rod (190) and the pawl (220) can be formed as a single piece or separate pieces that are connected together. The rod (190) is preferably rigid and does not bend. The rod (190) and pawl (220) can be located in a position relative to the wheel (90) so the pawl (220) engages a gear tooth (100) in the wheel (90). The rod (190) and pawl (220) can be located in a position relative to the wheel (90) to rotate the wheel (90) in a clockwise or counter-clockwise direction.

Dose Counter—Display Means

The housing (50) has a portal (250) for viewing the alpha-numerical characters on the wheel (90) (FIGS. 1 and 2). If the housing is transparent, the alpha-numerical characters on the wheel can be viewed through the housing wall.

The pMDI system of the present invention is assembled by placing the transparent canister (10), closed at one end with the valve assembly (30), in the housing (50). The canister (10) is placed in the housing (50) in a valve-stem (40) down position. The housing (50) comprises the dose counter. During the operation of the dose counter, the off-set mouthpiece (80) is placed in the patient's mouth and the canister (10) is depressed to dispense a dose of the medicament. Depressing the canister (10) causes the canister (10) to press downward on the rod (190) and pawl (220). The end of the pawl (220) is engaged with a gear tooth (100) in the wheel (90). The downward motion of the rod (190) and pawl (220) incrementally rotates the wheel (90) thereby moving a successive alpha-numeric character in position to be viewed in the portal (250). When the patient releases the canister (10), the canister moves upward to return to its original position. The rod compression spring (200) moves the rod (190) upward which moves the pawl (220) upward to engage the next gear tooth (100).

When the patient has dispensed a pre-determined number of doses, the word "reorder" can be viewed in the portal. When the patient has dispensed the maximum number of doses, the word "end" can be viewed in the portal. To determine the approximate number of doses remaining, the patient can remove the canister from the housing to observe the amount of medicament remaining in the canister. The canister need not be removed from the housing but can be observed through the housing if the housing is formed from a transparent material.

Dust Cap

The pMDI system of the present invention comprises a dust cap (85) (FIG. 1). The dust cap (85) can be separate from the housing (50). The dust cap (85) is shaped and sized to fit on the off-set mouthpiece (80) when the pMDI system is not in use. The dust cap (85) can be formed from plastic. It is well known in the art how to select the material, shape and size of the dust cap (85).

What is claimed is:

1. A pressurized metered dose inhaler system for dispensing multiple metered doses of a medicament to a patient, comprising:
    a) a transparent or partially transparent canister for containing the medicament and at least one propellant, wherein the canister is closed at one end with a metered dose valve assembly;
    b) a housing comprising a bottom and a top, the bottom being attached to a longitudinally-extending wall forming a cavity which is open at the top, wherein the bottom includes an orifice box for receiving the metered dose valve assembly, and the orifice box includes an internal stop which engages the metered dose valve assembly;
    c) a rotation means comprising a wheel rotatably mounted on the longitudinally-extending wall of the housing, wherein the wheel comprises a plurality of gear teeth between two raised rails on the face of the wheel, and wherein the gear teeth and two raised rails are concentric and are mounted perpendicular to the face of the wheel;
    d) a drive means for rotating the rotation means incrementally when the canister is depressed towards the internal stop and the valve assembly is actuated, wherein the drive means is mounted on the bottom of the housing and comprises a vertical rod connected with an angled flexible pawl, wherein the rod engages the canister and the pawl engages one of the gear teeth, and wherein the drive means moves down in response to depressing the canister onto the vertical rod, thereby incrementally rotating the rotation means;
    e) a counting means comprising alpha-numeric characters on the face of the wheel, wherein the alpha-numeric characters are incrementally advanced in response to rotating the rotation means; and
    f) a display means for viewing the counting means, wherein the display means is located in the longitudinally-extended wall of the housing; and
    g) a reverse rotation prevention means to prevent reverse rotation of the rotation means.

2. The system of claim 1, wherein the transparent or partially transparent canister is polymethyl methacrylate (PMMA), polystyrene, or polycarbonate.

3. The system of claim 1, wherein the transparent or partially transparent canister is acrylic glass.

4. The system of claim 1, wherein the transparent or partially transparent canister is double tough glass.

5. The system of claim 1, wherein the transparent or partially transparent canister is clear and colorless, clear and colored, partially clear and colorless, or partially clear and colored.

6. The system of claim 1, wherein the transparent or partially transparent canister withstands vapor pressures of about 85 psi.

7. The system of claim 1, wherein the transparent or partially transparent canister comprises measurement markings.

8. The system of claim 1, wherein the plurality of gear teeth is a number of gear teeth which is determined by the number of doses of medicament to be dispensed by the system.

9. The system of claim 1, wherein the drive means comprises a vertical spring-biased rod connected with an angled, elongated, flexible pawl.

10. The system of claim 1, wherein the end of the rod which engages the canister is enlarged.

11. The system of claim 10, wherein enlarged end of the rod is coated with or formed from non-slip material.

12. The system of claim 1, wherein the display means is a portal in the longitudinally-extended wall of the housing.

13. The system of claim 1, wherein the display means is a transparent or partially transparent longitudinally-extended wall of the housing.

14. The system of claim 1, wherein the reverse rotation prevention means is a stop projection on one face of the wheel and a plurality of stop projections on the inside of the housing.

15. The system of claim 1, wherein the counting means is a count-down or a count-up counter.

16. The system of claim 1, wherein the medicament a respiratory disease medicament.

17. The system of claim 1, wherein the propellant is 1,1,1,2-tetrafluoroethane or 1,1,1,2,3,3,3-heptafluoropropane.

18. The system of claim 1, further comprising an audible alarm.

* * * * *